(12) United States Patent
Eggink et al.

(10) Patent No.: US 9,351,451 B2
(45) Date of Patent: May 31, 2016

(54) RESISTANCE AGAINST *LEVEILLULA TAURICA* IN PEPPER

(71) Applicant: RIJK ZWAAN ZAADTEELT EN ZAADHANDEL B.V., De Lier (NL)

(72) Inventors: Pieter Martijn Eggink, Oostvoorne (NL); Björn Benny D'hoop, Rijswijk ZH (NL); Marjolein Brouwer, Dussen (NL); Antoine Xavier Deniau, Rocheford du Gard (FR)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 378 days.

(21) Appl. No.: 13/837,989

(22) Filed: Mar. 15, 2013

(65) Prior Publication Data

US 2014/0272088 A1     Sep. 18, 2014

(51) Int. Cl.
*A01H 5/08*     (2006.01)
*A01H 1/04*     (2006.01)
*C12Q 1/68*     (2006.01)

(52) U.S. Cl.
CPC ............... *A01H 5/08* (2013.01); *C12Q 1/6895* (2013.01); *C12Q 2600/13* (2013.01)

(58) Field of Classification Search
None
See application file for complete search history.

(56) References Cited

PUBLICATIONS

Daubeze et al. Plant Breeding 114: 327-332 (1995).*
Lefebvre et al. Theoretical and Applied Genetics 107(4): 661-666 (2003).*
Hossain et al. Japanese Journal of Tropical Agriculture 47(1): 9-16 (2003).*
de Souza et al. Plant Pathology 52(5): 613-619 (2003).*

* cited by examiner

*Primary Examiner* — David T Fox
(74) *Attorney, Agent, or Firm* — Vedder Price P.C.; Thomas J. Kowalski; Deborah L. Lu

(57) ABSTRACT

The present invention relates to a pepper plant (*Capsicum* spec.) showing resistance against *Leveillula taurica*, wherein the pepper plant may comprise a QTL on LG1/8 which QTL leads to resistance against *Leveillula taurica* and wherein the said QTL is as present in or obtainable from a pepper plant, representative seed of which was deposited under deposit accession number NCIMB 42136. Preferably, the QTL is homozygously present. In the seeds of the deposit the QTL is linked to a molecular marker according to SEQ ID NO 1.

13 Claims, No Drawings

RESISTANCE AGAINST *LEVEILLULA TAURICA* IN PEPPER

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to plants which express resistance against a pathogen. More in particular, this invention relates to pepper plant which is resistant against *Leveillula taurica*. Furthermore the invention relates to the seeds, progeny and propagation material derived from the resistant pepper plant and the use of the resistant plant as germplasm in a breeding program.

BACKGROUND OF THE INVENTION

Sweet pepper plants belong to the genus *Capsicum* which is part of the Nightshade family (Solanaceae). *Capsicum* species are native to South America, Middle America and a part of North America, where they have been cultivated for thousands of years, and are now cultivated worldwide. Some of the members of *Capsicum* are used as spices, vegetables, and medicines.

The fruit of *Capsicum* plants have a variety of names depending on place and type. The species *Capsicum annuum* is the most common and extensively cultivated of the five domesticated *Capsicum* species (*Capsicum annuum, Capsicum baccatum, Capsicum chacoense, Capsicum chinense, Capsicum frutescens*). It may comprise several cultivar groups among which bell pepper (also named paprika or sweet pepper) is the most commonly grown in northern Europe and the USA. Bell peppers are eaten raw, cooked, immature and mature and may be processed into powders, sauces, and salsas. The fruits are mostly green in the beginning, but during ripening they become red, yellow, orange, purple, white or brown.

Peppers may be cultivated in the open field, greenhouses or shade house under a wide range of various climatic conditions, but they will be most successful in warm and dry conditions.

Powdery mildew infections in pepper caused by *Leveillula taurica* are becoming an increasing problem in pepper production areas. *Leveillula taurica* causes powdery mildew of numerous crops as pepper, tomato, artichoke, cucumber, onion and potato.

The geographical distribution of *Leveillula* centers in central and western Asia, and in the Mediterranean region. The first symptoms of the disease are yellow necrotic spots developing on the oldest leaves, later also on younger leaves. On the lower surface of the infected leaves white sporulating areas with abundant conidia are visible. The disease eventually leads to defoliation. Powdery mildew infections in pepper fields may lead to serious yield reduction. Forecasting and managing powdery mildew epidemics is difficult, the latter due to intercellular growth of the fungus. Chemical control is therefore non-successful so solutions are sought in the area of genetic control.

Resistance sources identified in *Capsicum* spec. L. are rare and unsatisfactory. Several pepper accessions exhibit various levels of resistance in natural infection conditions although most of them are non-*annuum* species or their resistance level is low. Only few articles and reports on resistance in pepper to *Leveillula taurica* may be found.

The most promising source of resistance was found in the *C. annuum* accession "H3" from east Africa (Daubeze et al, 1989). Research on the hereditary nature of the underlying resistance factors done by Daubeze et al. (1995) (Plant Breeding 114, 327-332) and Lefebvre et al. (2003) (Theoretical and Applied Genetics, 107:661-66) show that the genetics underlying the *L. taurica* resistance is complicated. In a population made by a cross between "H3" and the susceptible bell-pepper Vania, five genomic regions were found, P5, P6, P9, P10, and P12 with additive QTL's which were involved in contributing to the found resistance. Two genomic regions were common to both the evaluation methods, whereas other QTLs were method-specific, reflecting the environment dependence of powdery mildew epidemics. The individual QTL which could explain most of the found variance (26%) was located at P6 (Lefebvre et al. 2003, supra).

Because in the current state of the art no pepper varieties are known that are highly resistant to *Leveillula taurica*, it is the object of the present invention to provide a pepper plant with resistance to *Leveillula taurica*.

Citation or identification of any document in this application is not an admission that such document is available as prior art to the present invention.

SUMMARY OF THE INVENTION

In the research that led to the present invention pepper plants were developed that are highly resistant against *L. taurica*. The said resistance of the invention is controlled by a genetic determinant, the inheritance of which is consistent with that of a polygenic recessive trait. 'Recessive trait' in this case means that the achievable resistance is only observable in plants which may comprise the genetic determinant in homozygous state, whereas plants which may comprise the genetic determinant in heterozygous state do not show resistance.

In the present invention a genetic determinant that consists of a QTL was found that alone explains 56.8% of the found variance in resistance as described in the experiments (Example 2) and is located on LG1/8.

LG1/8 is an additional linkage group for chromosome 1 and chromosome 8. A special notation is used, because of the known reciprocal translocation in that region, differentiating the genome of *C. annuum* from that of other *Capsicum* species.

Until now, there is no publication known on a QTL on LG1/8 in pepper conferring resistance to *L. taurica*. Neither are any data known on QTL's conferring resistance to *L. taurica* with that level of explained variation. Daubeze et al. (1995, supra) showed that the more severe the infection, the more genes or gene combinations are necessary to confer resistance.

The current invention which relates to a QTL that explains almost 57% of the found variation has certainly an added value compared to this prior art. When plant material is used in a breeding program, the use of a QTL that may explain most of the variance found in resistance against *Leveillula taurica* may provide a more efficient method than the combined use of several QTL's that may explain less of the found variance. In an early stage of growing plants, a strong QTL may provide a good indicator of the phenotypic trait without the necessity of doing a more time and cost consuming PM test. The less different QTL's are needed the more efficient a test may be applied. The more variance a QTL may explain, the more predictive power and therefore the more value a QTL has.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT INFORMATION

Representative seeds of pepper plants of the invention that carry the QTL as described herein were deposited under NCIMB deposit accession number 42136 on 14 Mar. 2013 with NCIMB Ltd. (Ferguson Building, Craibstone Estate, Bucksburn, Aberdeen, AB21 9YA) and NCIMB 41789 on 25 Nov. 2010.

The deposits with NCIMB, under deposit accession number NCIMB 42136 on 14 Mar. 2013 and NCIMB 41789 on 25 Nov. 2010 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention thus relates to a pepper plant (*Capsicum* spec.) showing resistance against *Leveillula taurica*, wherein the pepper plant may comprise a QTL on LG1/8 which QTL when homozygously present, leads to resistance against *Leveillula taurica* and wherein the said QTL is as present in or obtainable from a pepper plant representative seed of which was deposited under deposit accession number NCIMB 42136.

In the seeds of the deposit the QTL is linked to a molecular marker according to SEQ ID NO. 1. Plants of the invention may or may not have the molecular marker. If the plant does not have the molecular marker but when the QTL is present such a plant is still a pepper plant of the invention.

In a preferred embodiment the QTL is homozygously present and the pepper plant shows resistance against *Leveillula taurica*. Plants in which the QTL is heterozygously present are also part of this invention since although they may not show the resistance phenotype, such plants are still a source of the QTL and may be used in breeding for *Leveillula taurica* resistant peppers.

A pepper plant of the invention is obtainable by:
a) crossing a first pepper plant with a second pepper plant, wherein at least one of the said plants is grown from seed, of which a representative sample was deposited under deposit number NCIMB 42136, or a progeny plant thereof,
b) selfing the resulting F1 plants to obtain a F2 population, and
c) identifying and selecting plants from the F2 population that have the QTL on LG1/8 that leads to resistance against *Leveillula taurica*.

The invention provides furthermore a pepper plant, which may comprise the QTL homozygously and has a powdery mildew resistance score that is on average in order of increased preference at least 1.5 lower, at least 1.7 lower, at least 1.9 lower, at least 2.1 lower, at least 2.3 lower, at least 2.5 lower at least 2.6 lower, on a scale of 0 to 5, compared to the powdery mildew resistance score of a pepper plant not comprising the QTL.

According to a further aspect thereof the invention provides a pepper seed, which may comprise the QTL as defined herein. The plant that may be grown from the seed may comprise the QTL located on LG 1/8 and when homozygously present the plant shows resistance against *Leveillula taurica*.

The invention also relates to progeny of a pepper plant, or of pepper seed as described herein, which progeny may comprise the QTL on LG 1/8 as defined herein, and wherein the progeny plant is resistant to *Leveillula taurica* when the QTL is homozygously present.

The invention further provides propagation material derived from a plant of the invention or of pepper seed of the invention, wherein the propagation material may comprise the QTL on LG1/8 and wherein the plant grown from the propagation material is resistant to *Leveillula taurica* when the QTL is homozygously present.

The propagation material is suitably selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof. A pepper fruit which may comprise the QTL as defined herein is also part of this invention.

Furthermore, a food product is provided which is made of a fruit of the invention or is made of parts thereof, or a processed food product made thereof, wherein the product may comprise the QTL that leads to resistance against *Leveillula taurica* as defined herein.

According to a further aspect thereof the invention relates to a nucleic acid which is causative of resistance to *Leveillula taurica* which may comprise a DNA sequence, which is located on LG1/8 and linked to a molecular marker according to SEQ ID NO. 1, or a part thereof.

Furthermore, the invention relates to the use of a molecular marker for identifying a QTL located on Linkage Group LG1/8 in a pepper genome and conferring resistance against *Leveillula taurica*, wherein the molecular marker comprise a part or the whole of SEQ ID NO. 1.

The use of the marker of SEQ ID NO. 1 or the nucleic acid that is causative of the resistance to identify or develop other pepper plants with resistance against *Leveillula taurica* or to identify or develop other markers linked to the QTL on LG1/8 is also part of this invention.

In addition, the invention relates to the use of the plant that has the resistance against *Leveillula taurica* of the invention as germplasm in a breeding program for the development of pepper plants that are resistant against *Leveillula taurica*.

The pepper plants according to the invention may grow the following fruit types: sweet pepper including pepper, bell pepper, big rectangular pepper, conical pepper, long conical pepper or blocky-type pepper.

The fruits of the pepper plants according to the invention at maturity may be a green, yellow, orange, red, ivory, brown, or purple fruit.

In one embodiment, the pepper plant of the invention is a representative of one of the following species: *Capsicum annuum, Capsicum baccatum, Capsicum chacoense, Capsicum chinense, Capsicum frutescens*, or any hybrid combination thereof. These species are the most commonly used breeds and in addition may easily be crossed amongst each other, thus facilitating obtaining a plant showing the *Leveillula taurica* resistance trait of the invention.

The invention further relates to seed of the pepper plants of the invention and to other parts of the plant that are suitable for sexual reproduction, i.e. propagation material. Such parts are for example selected from the group consisting of microspores, pollen, ovaries, ovules, embryo sacs and egg cells.

In addition, the invention relates to parts of the plant that are suitable for vegetative reproduction, in particular cuttings, roots, stems, cells, protoplasts, and tissue culture of the pepper plants of the invention. The tissue culture may comprise regenerable cells. Such a tissue culture may be derived from leaves, pollen, embryos, cotyledon, hypocotyls, meristematic cells, roots, root tips, anthers, flowers, seeds and stems.

The invention also relates to progeny of the pepper plants of the invention. Such progeny may be produced by sexual or vegetative reproduction of a plant of the invention or a progeny plant thereof. The regenerated progeny plant shows resistance to *Leveillula taurica* in the same or a similar way as the plants, of which representative seed was deposited. This means that such progeny has the same characteristics as claimed for the pepper plants of the invention. In addition to this, the plant may be modified in one or more other characteristics. Such additional modifications are for example effected by mutagenesis or by transformation with a transgene.

The invention, furthermore, relates to hybrid seed and to a method of producing hybrid seed which may comprise crossing a first parent plant with a second parent plant and harvesting the resultant hybrid seed. In case the trait is recessive, both parent plants need to be homozygous for the resistance trait in order for the hybrid seed to carry the trait of the invention. They need not necessarily tebe uniform for other traits.

It is clear that a parent that provides the trait of the invention is not necessarily a plant grown directly from the deposited seeds. The parent may also be a progeny plant from the seed or a progeny plant from seeds that are identified to have or to have acquired the trait of the invention by other means.

In one embodiment, the invention relates to pepper plants that carry the resistance trait of the invention and having acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic information leading to the *Leveillula* resistance is acquired is formed by plants grown from the deposited seeds or sexual or vegetative descendants therefrom.

The invention also relates to the germplasm of plants of the invention. The germplasm is constituted by all inherited characteristics of an organism and according to the invention encompasses at least the *Leveillula* resistance trait of the invention.

The invention further relates to cells of the pepper plants that show the resistance to *Leveillula taurica*. Each cell of such pepper plants carries the genetic information that leads to phenotypic expression of said resistance trait. The cell may be an individual cell or be part of a pepper plant or pepper plant part.

The invention also relates to the pepper fruits that are produced by the plants of the invention. In addition, the invention relates to parts of the pepper fruits and processed products produced from the pepper fruits. The fruits and products derived therefrom carry the *Leveillula* resistance conferring QTL of the invention.

In one aspect the invention relates to a method for production of a pepper plant which has the trait of resistance against *Leveillula taurica*, which may comprise
  a) crossing a plant which may comprise a QTL that leads to the *Leveillula* resistance trait with another plant;
  b) selfing the resulting F1 for obtaining F2 plants;
  c) selecting plants that have the *Leveillula* resistance trait in the F2;
  d) optionally performing one or more additional rounds of selfing or crossing, and subsequently selecting, for a plant which may comprise/showing the *Leveillula* resistance trait of the invention.

The word "trait" in the context of this application refers to the phenotype of the plant. In particular, the word "trait" refers to the trait of the invention, more in particular to the trait of resistance against *Leveillula taurica*. The terms "genetic determinant" or "QTL" are used for the genetic information in the genome of the plant that causes the trait of the invention. When a plant shows the trait of the invention, its genome may comprise the QTL causing the trait of the invention. The plant thus has the QTL of the invention.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a pepper plant which has the trait of resistance against *Leveillula taurica*, which may comprise
  a) crossing a plant which may comprise the QTL that leads to the *Leveillula* resistance trait with another plant;
  b) optionally backcrossing the resulting F1 with the preferred parent;
  c) selecting for plants that have the *Leveillula* resistance trait in the F2;

d) optionally performing one or more additional rounds of selfing or crossing, and subsequently selecting, for a plant which may comprise the *Leveillula* resistance trait.

The invention additionally provides a method of introducing another desired trait into a pepper plant which has the trait of resistance against *Leveillula taurica*, which may comprise:
a) crossing a pepper plant that has the trait of resistance against *Leveillula taurica*, representative seed of which were deposited under deposit number NCIMB 42136, with a second pepper plant that may comprise another desired trait to produce F1 progeny;
b) selecting an F1 progeny that may comprise said trait of resistance against *Leveillula taurica* and the other desired trait;
c) crossing the selected F1 progeny with either parent, to produce backcross progeny;
d) selecting backcross progeny which may comprise the other desired trait and the trait of resistance against *Leveillula taurica*; and
e) optionally repeating steps c) and d) one or more times in succession to produce selected fourth or higher backcross progeny that may comprise the other desired trait and the trait of resistance against *Leveillula taurica*. The invention includes a pepper plant produced by this method.

In one embodiment selection for plants having the trait of resistance against *Leveillula taurica* is done in the F1 or any further generation by using the molecular marker according to SEQ ID NO. 1. In another aspect selection for the trait of the invention is started in the F2 of a cross or alternatively of a backcross. Selection of plants in the F2 may be done phenotypically as well as by using the marker(s) which directly or indirectly detect the QTL underlying the trait.

In one embodiment selection for plants having the trait of resistance against *Leveillula taurica* is started in the F3 or a later generation.

In one embodiment the plant which may comprise the QTL is a plant of an inbred line, a hybrid, a doubled haploid, or of a segregating population.

The invention further provides a method for the production of a pepper plant having the trait of resistance against *Leveillula taurica* by using a doubled haploid generation technique to generate a doubled haploid line which may comprise the said trait.

The invention furthermore relates to hybrid seed that may be grown into a plant having the trait of resistance against *Leveillula taurica* and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid pepper plant that has the trait of resistance against *Leveillula taurica*, which may comprise crossing a first parent pepper plant with a second parent pepper plant and harvesting the resultant hybrid seed, of which the first parent plant and/or the second parent plant has the trait of resistance against *Leveillula taurica*, and growing said hybrid seeds into hybrid plants having the trait of resistance against *Leveillula taurica*.

The invention also relates to a method for the production of a pepper plant having the trait of resistance against *Leveillula taurica* by using a seed that may comprise a QTL in its genome that leads to the trait of resistance against *Leveillula taurica* for growing the said pepper plant. The seeds are suitably seeds of which a representative sample was deposited with the NCIMB under deposit number NCIMB 42136.

The invention also relates to a method for seed production which may comprise growing pepper plants from seeds of which a representative sample was deposited with the NCIMB under deposit number NCIMB 42136, allowing the plants to produce seeds, and harvesting those seeds. Production of the seeds is suitably done by crossing or selfing.

In one embodiment, the invention relates to a method for the production of a pepper plant having the trait of resistance against *Leveillula taurica* by using tissue culture.

The invention furthermore relates to a method for the production of a pepper plant having the trait of resistance against *Leveillula taurica* by using vegetative reproduction.

In one embodiment, the invention relates to a method for the production of a pepper plant having the trait of resistance against *Leveillula taurica* by using a method for genetic modification to introduce or introgress the said trait into the pepper plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of pepper plants that have the trait of resistance against *Leveillula taurica* wherein germplasm which may comprise said trait is used. Representative seed of a plant which may comprise the QTL and being representative for the germplasm was deposited with the NCIMB under deposit number NCIMB 42136.

In a further embodiment the invention relates to a method for the production of a pepper plant having the trait of resistance against *Leveillula taurica* wherein progeny or propagation material of a plant which may comprise the QTL conferring said trait is used as a source to introgress the said trait into another pepper plant. Representative seed of said plant which may comprise the QTL was deposited with the NCIMB under deposit number NCIMB 42136.

The invention provides preferably a pepper plant having the trait of resistance against *Leveillula taurica*, which plant is obtainable by any of the methods herein described and/or familiar to the skilled person.

The invention relates to a cell of a pepper plant (*Capsicum* spec.), which pepper plant shows the resistance to *Leveillula taurica* as found in a pepper plant grown from seed as deposited under NCIMB accession number 42136.

The invention also relates to a cell of a pepper plant (*Capsicum* spec.), which pepper plant shows the resistance to *Leveillula taurica* as found in a pepper plant grown from seed as deposited under NCIMB accession number 42136, which pepper plant is obtainable by crossing a pepper plant with a pepper plant grown from seed as deposited under NCIMB accession number 42136, and selecting for a pepper plant that shows resistance to *Leveillula taurica*.

In one embodiment the invention relates to the use of seeds that were deposited under NCIMB accession number 42136, for transferring the resistance to *Leveillula taurica* of the invention into another pepper plant (*Capsicum* spec.).

In another embodiment the invention relates to the use of a pepper plant (*Capsicum* spec.) which pepper plant shows resistance to *Leveillula taurica* as found in a pepper plant grown from seed as deposited under NCIMB accession number 42136, as a crop.

The invention also relates to the use of a pepper plant (*Capsicum* spec.) which shows the resistance to *Leveillula taurica* as found in a pepper plant grown from seed as deposited under NCIMB accession number 42136, as a source of seed.

Further, the invention relates to the use of a pepper plant (*Capsicum* spec.) which shows resistance to *Leveillula taurica* as found in a pepper plant grown from seed as deposited under NCIMB accession number 42136, as a source of propagating material.

Moreover, the invention relates to the use of a pepper plant (*Capsicum* spec.) which shows the resistance to *Leveillula taurica* as found in a pepper plant grown from seed as deposited under NCIMB accession numbers 42136, for consumption.

The invention also relates to the use of the resistance alleles as found in seeds that were deposited under NCIMB accession number 42136, for conferring resistance against *Leveillula taurica* on a pepper plant (*Capsicum* spec.).

Furthermore, the invention relates to the use of a pepper plant (*Capsicum* spec.) as a donor of resistance alleles as found in seeds that were deposited under NCIMB accession number 42136.

DEFINITIONS

"Introgression" as used in this application is intended to mean introduction of a trait into a plant not carrying the trait, by means of crossing and selection.

"Progeny" as used in this application is intended to mean the first and all further descendants from a cross with a plant of the invention that shows fruit formation in the absence of fertilisation. Progeny of the invention are descendants of any cross with a plant of the invention that carries the trait that leads to fruit formation in the absence of fertilisation.

"Progeny" also encompasses plants that carry the trait of the invention and are obtained from other plants of the invention by vegetative propagation or multiplication.

An ancestor is intended to encompass not only the generation immediately prior to the plant but also multiple generations before that. More in particular, the ancestor is a plant from the deposited seed or a further generation descendent there from.

Marker Data

TABLE 1

Sequence of marker linked to QTL on LG1/8

| | |
|---|---|
| SEQ ID NO. 1 | CCCGAGGTAGACATCATACGAGGAGAATTTCCTGCT AAAATTGAGTTGTT[T/C]TGTCAGAGGAGTCGCTCAC ATGATAAGTATGTTGGCGAGTTAGACCTCAT |

The invention will be further illustrated by the examples that follow, which are given for illustration purposes only and are not intended to limit the invention in any way.

EXAMPLES

Example 1

Resistance Assay *Leveillula taurica*

In order to identify whether pepper plants have resistance to *Leveillula taurica*, seeds of different pepper plant lines are sown and grown for 6 weeks. From 6 weeks on, plants are inoculated by spraying the plants with a suspension containing 15.000-50.000 *Leveillula taurica* spores per ml. This spraying is repeated several times to ensure sufficient disease pressure/pathogenic stress. To assess the infection affecting the plants the disease scale adapted from Daubeze et al. (1995, supra) was used. The sporulation intensity was assessed on infected plant leaves, according to a semi-quantitative scale with:

0=no visible sporulation
1=weak or no sporulation
2=several isolated sporulation sites covering less than 25% of the lower leaf area
3=numerous sporulation sites covering up to 50% of the lower leaf area
4=numerous coalescent sporulation sites covering up to 75% of the lower leaf area
5=the whole surface of the leaf covered with dense sporulations

Example 2

Identification of QTL LG1/8

A mapping population was made from a cross between *C. frutescens* as deposited at the NCIMB under accession number 41789 and a susceptible *C. annuum* line. The initial population consisted of about 100 lines. For marker development and the construction of a genetic map 76 lines and the two parent lines were genotyped with more than 5000 SNPs. Polymorphic markers were used to develop a population specific map. Phenotypic data has been collected on this population for the trait *Leveillula taurica* resistance. Plants were tested for resistance against *Leveillula taurica* according to the method as described in example 1. A total of 7 plants per line were tested and the powdery mildew infection level per line was determined. The overlap between phenotypic data and genotypic data resulted in a set of 70 lines to be analyzed with the software package MapQTL.

As a start an interval mapping analysis was performed using the regression algorithm. This was followed by a permutation test to derive the LOD threshold, above which a marker locus is considered a significant QTL. For the *Leveillula taurica* resistance in this test, the threshold was found to be 3.6. Subsequently the interval mapping results were inspected using the data-driven thresholds and each time the marker closest to a significant peak was chosen as cofactor for a following round of MQM mapping until stable peaks were observed.

A QTL causing the trait of resistance against *Leveillula taurica* was found to reside on the linkage group 1/8. This QTL could explain 56.8% of the found variation in *Leveillula*. The LOD score for the QTL is 17.59.

Table 2 shows the resistance scores of 70 plant lines of the mapping population with and without the QTL on LG1/8. As the results in Table 2 show, the average score of pepper plant lines which may comprise the QTL is 0.60 on a scale of 0 to 5. The average score of plant lines without the QTL is 2.97. The difference between the average of the two groups is 2.37 on a scale of 0 to 5.

TABLE 2

*Leveillula taurica* resistance scores for 70 different plant lines of the mapping population with and without the QTL on LG1/8

| Plant line | Resistance score | QTL present (A allele) | Plant line | Resistance score | QTL not present (B allele) |
|---|---|---|---|---|---|
| line 6 | 1 | A | line 1 | 2 | B |
| line 8 | 0 | A | line 2 | 3 | B |
| line 9 | 1 | A | line 3 | 2 | B |
| line 11 | 2 | A | line 4 | 3 | B |

TABLE 2-continued

*Leveillula taurica* resistance scores for 70 different plant lines of the mapping population with and without the QTL on LG1/8

| Plant line | Resistance score | QTL present (A allele) | Plant line | Resistance score | QTL not present (B allele) |
|---|---|---|---|---|---|
| line 12 | 1 | A | line 5 | 5 | B |
| line 13 | 0 | A | line 7 | 1 | B |
| line 15 | 0 | A | line 10 | 5 | B |
| line 19 | 0 | A | line 14 | 3 | B |
| line 21 | 0 | A | line 16 | 2 | B |
| line 24 | 1 | A | line 17 | 2 | B |
| line 26 | 0 | A | line 18 | 3 | B |
| line 27 | 0 | A | line 20 | 2 | B |
| line 33 | 1 | A | line 22 | 1 | B |
| line 34 | 1 | A | line 23 | 5 | B |
| line 35 | 0 | A | line 25 | 3 | B |
| line 36 | 2 | A | line 28 | 3 | B |
| line 37 | 1 | A | line 29 | 2 | B |
| line 38 | 0 | A | line 30 | 4 | B |
| line 40 | 0 | A | line 31 | 2 | B |
| line 41 | 0 | A | line 32 | 4 | B |
| line 42 | 1 | A | line 39 | 3 | B |
| line 44 | 0 | A | line 43 | 3 | B |
| line 45 | 1 | A | line 47 | 3 | B |
| line 46 | 0 | A | line 48 | 3 | B |
| line 49 | 0 | A | line 50 | 5 | B |
| line 51 | 1 | A | line 52 | 4 | B |
| line 53 | 2 | A | line 55 | 2 | B |
| line 54 | 1 | A | line 57 | 4 | B |
| line 56 | 0 | A | line 60 | 4 | B |
| line 58 | 0 | A | line 62 | 3 | B |
| line 59 | 0 | A | line 63 | 1 | B |
| line 61 | 3 | A | line 65 | 4 | B |
| line 64 | 0 | A | line 67 | 5 | B |
| line 66 | 1 | A | line 68 | 1 | B |
| line 69 | 0 | A | line 70 | 2 | B |
| Average | 0.60 | A | Average | 2.97 | B |

Example 3

Heritability of the Resistance Trait and the QTL on LG1/8

To validate the effect that the QTL on LG 1/8 has on the resistance against *Leveillula taurica* by pepper plants as described in Example 2 and Table 2, an internal pepper plant line containing the QTL that confers resistance against *L. taurica* was crossed with another internal pepper plant line not containing the said QTL. Plants from the F2 population that originated from this cross were tested for the presence of the QTL on LG1/8 with a marker designed based on sequence SEQ ID NO. 1 as shown in Table 1. Only plants that were homozygous for the marker were tested on resistance against *Leveillula taurica* according to the method described in Example 1.

In Table 3, the resistance scores for individual plants from the F2 with and without the QTL are given. As shown in Table 3, the average score of pepper plants from the F2 which may comprise the QTL is 2.44 on a scale of 0 to 5. The average score of pepper plants from the F2 without the QTL is 4.68. The difference between these two groups is 2.24 on a scale of 0 to 5.

The same test and analysis as described for the plants from the F2 population was done on plants from 3 different F2BC1 derived from said F2 population. Here, the difference of the group average resistance score between the group of plants with the QTL and without the QTL was respectively 2.00, 2.59 and 2.08.

TABLE 3

Resistance scores (classes 0-5) for individual plants of a F2 population, with and without the QTL

| Plant code | Resistance score | QTL present (A allele) | Plant code | Resistance score | QTL not present (B allele) |
|---|---|---|---|---|---|
| 103 | 0 | A | 59 | 5 | B |
| 172 | 2 | A | 76 | 5 | B |
| 36 | 1 | A | 80 | 4 | B |
| 107 | 3 | A | 32 | 5 | B |
| 183 | 4 | A | 35 | 5 | B |
| 108 | 1 | A | 43 | 5 | B |
| 194 | 1 | A | 29 | 5 | B |
| 64 | 2 | A | 50 | 5 | B |
| 81 | 5 | A | 69 | 5 | B |
| 85 | 1 | A | 49 | 5 | B |
| 179 | 2 | A | 70 | 4 | B |
| 180 | 4 | A | 44 | 5 | B |
| 174 | 5 | A | 75 | 5 | B |
| 91 | 0 | A | 84 | 4 | B |
| 41 | 3 | A | 100 | 3 | B |
| 34 | 3 | A | 109 | 4 | B |
| 62 | 4 | A | 40 | | B |
| 95 | 3 | A | 68 | 5 | B |
| | | | 45 | 5 | B |
| | | | 53 | 5 | B |
| Average | 2.44 | | Average | 4.68 | |

The invention is further described by the following numbered paragraphs.

1. A pepper plant (*Capsicum* spec.) showing resistance against *Leveillula taurica*, wherein the pepper plant may comprise a QTL on LG1/8 which QTL leads to resistance against *Leveillula taurica* and wherein the said QTL is as present in or obtainable from a pepper plant, representative seed of which was deposited under deposit accession number NCIMB 42136.

2. The pepper plant of paragraph 1, wherein the QTL is homozygously present.

3. The pepper plant as described in paragraph 1 or 2, wherein in the seeds of the deposit the QTL is linked to a molecular marker according to SEQ ID NO 1.

4. A pepper plant as described in any one of paragraphs 1-3, obtainable by:
   a) crossing a first pepper plant with a second pepper plant, wherein at least one of the said plants is grown from seed, of which a representative sample was deposited under deposit number NCIMB 42136, or a progeny plant thereof,
   b) selfing the resulting F1 plants to obtain a F2 population, and
   c) identifying and selecting plants from the F2 population that have the QTL on LG1/8 that leads to resistance against *Leveillula taurica*.

5. A pepper plant as described in any of the paragraphs 1-4, which may comprise the QTL homozygously and has a powdery mildew resistance score that is on average in order of increased preference at least 1.5 lower, at least 1.7 lower, at least 1.9 lower, at least 2.1 lower, at least 2.3 lower, at least 2.5 lower, at least 2.6 lower, on a scale of 0 to 5, than the powdery mildew resistance score of a pepper plant not comprising the QTL.

6. Pepper seed which may comprise the QTL as defined in any of the paragraphs 1-2.

7. Seed of a pepper plant as defined in any of the paragraphs 1-5, wherein the plant that may be grown from the seed may comprise the QTL located on LG 1/8 as defined in any of the paragraphs 1-2 and wherein the plant shows resistance against *Leveillula taurica*.

8. Progeny of a pepper plant as described in any one of the paragraphs 1-5, or of pepper seed as described in paragraph 6 or 7, which may comprise the QTL on LG 1/8 as defined in any of the paragraphs 1-2, and wherein the progeny plant is resistant to *Leveillula taurica*.

9. Propagation material derived from a plant as described in any of the paragraphs 1-5 or of pepper seed as described in paragraph 6 or 7, wherein the propagation material may comprise the QTL on LG1/8 and wherein the plant grown from the propagation material is resistant to *Leveillula taurica*, and wherein the propagation material is preferably selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

10. A pepper fruit which may comprise the QTL as defined in any of the paragraphs 1-2.

11. A food product made of a fruit as described in paragraph 10 or made of parts thereof, or a processed food product made thereof, which may comprise the QTL as defined in any of the paragraphs 1-2.

12. A nucleic acid which is causative of resistance to *Leveillula taurica* which may comprise a DNA sequence, which is located on LG1/8 and linked to a molecular marker according to SEQ ID NO 1, or a part thereof.

13. Use of a molecular marker for identifying a QTL located on Linkage Group LG1/8 in a pepper genome and conferring resistance against *Leveillula taurica*, wherein the molecular markers comprise a part or the whole of SEQ ID NO 1.

14. Use of the marker as described in paragraph 13 or the nucleic acid as described in paragraph 12 to identify or develop other pepper plants with resistance against *Leveillula taurica* or to identify or develop other markers linked to the QTL on LG1/8 as defined in paragraph 1 or 2.

15. Use of the plant as described in any of the paragraphs 1-5 as germplasm in a breeding program for the development of pepper plants that are resistant against *Leveillula taurica*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Capsicum annuum* plant showing resistance against *Leveillula taurica*, wherein the *Capsicum annuum* plant comprises a QTL on LG1/8 which leads to resistance against *Leveillula taurica* and wherein the QTL is as found in a source plant, wherein seed of said source plant was deposited under deposit accession number NCIMB 42136.

2. The *C. annuum* plant of claim 1, wherein the QTL is homozygously present.

3. The *C. annuum* plant of claim 1, wherein in the seeds of the deposit, the QTL is linked to a molecular marker according to SEQ ID NO 1, wherein the nucleotide at position 51 of SEQ ID NO 1 is a C.

4. The *C. annuum* plant of claim 1, obtained by:
  a) crossing a first *C. annuum* plant with a second *C. annuum* plant, wherein at least one of the first and second plants is grown from a source seed, which source seed was deposited under deposit number NCIMB 42136, or a progeny *C. annuum* plant of a plant grown from said source seed, to obtain F1 plants,
  b) selfing the resulting F1 plants to obtain an F2 population, and
  c) identifying and selecting plants from the F2 population that have the QTL on LG1/8 that leads to resistance against *Leveillula taurica*.

5. The *C. annuum* plant of claim 1, which comprises the QTL homozygously and has a powdery mildew resistance score that is on average in order of increased preference at least 1.5 lower, at least 1.7 lower, at least 1.9 lower, at least 2.1 lower, at least 2.3 lower, at least 2.5 lower, at least 2.6 lower, on a scale of 0 to 5, than the powdery mildew resistance score of a pepper plant not comprising the QTL.

6. A *C. annuum* seed comprising the QTL of claim 1.

7. A seed of the *C. annuum* plant of claim 1, wherein the *C. annuum* plant that grows from the seed comprises the QTL of claim 1, and wherein the plant is resistant against *Leveillula taurica*.

8. A progeny *C. annuum* plant of the *C. annuum* plant of claim 1, wherein the progeny plant comprises the QTL on LG 1/8 of claim 1, and wherein the progeny plant is resistant to *Leveillula taurica*.

9. A propagation material derived from the *C. annuum* plant of claim 1, wherein the propagation material comprises the QTL on LG1/8 and wherein a plant grown from the propagation material is resistant to *Leveillula taurica*.

SEQUENCE LISTING

```
<160> NUMBER OF SEQ ID NOS: 1

<210> SEQ ID NO 1
<211> LENGTH: 101
<212> TYPE: DNA
<213> ORGANISM: Capsicum
<220> FEATURE:
<221> NAME/KEY: source
<222> LOCATION: 1..101
<223> OTHER INFORMATION: /organism="Capsicum"
      /mol_type="unassigned DNA"
<220> FEATURE:
<221> NAME/KEY: variation
<222> LOCATION: 51
<223> OTHER INFORMATION: /replace="c"

<400> SEQUENCE: 1
cccgaggtag acatcatacg aggagaattt cctgctaaaa ttgagttgtt ttgtcagagg      60
agtcgctcac atgataagta tgttggcgag ttagacctca t                        101
```

10. A *C. annuum* fruit comprising the QTL of claim 1.

11. A food product made of a fruit of claim 10 or made of parts thereof, or a processed food product made thereof, comprising the QTL of claim 1 or 3.

12. A method for identifying a QTL located on Linkage Group LG1/8 in a *C. annuum* genome and conferring resistance against *Leveillula taurica*, comprising identifying the QTL linked to a molecular marker, wherein the molecular marker comprises SEQ ID NO 1, wherein the nucleotide at position 51 of SEQ ID NO 1 is a C.

13. The propagation material of claim 9, wherein the propagation material comprises a callus, microspore, pollen, ovary, ovule, embryo, embryo sac, egg cell, cutting, root, cell, protoplast, leaf, cotyledon, hypocotyl, meristematic cell, root, root tip, microspore, anther, flower, seed or stems; or a part or tissue culture thereof.

\* \* \* \* \*